(12) United States Patent
Grossmann et al.

(10) Patent No.: US 10,143,402 B2
(45) Date of Patent: Dec. 4, 2018

(54) LENGTH MEASURING DEVICE

(71) Applicant: Seca AG, Reinbach (CH)

(72) Inventors: Jan-Erik Grossmann, Hamburg (DE); Björn Jensen, Hamburg (DE); Peter Lawitzke, Rethwisch (DE)

(73) Assignee: SECA AG (CH)

( * ) Notice: Subject to any disclaimer, the term of this patent is extended or adjusted under 35 U.S.C. 154(b) by 783 days.

(21) Appl. No.: 14/441,802

(22) PCT Filed: Aug. 14, 2013

(86) PCT No.: PCT/EP2013/067022
§ 371 (c)(1),
(2) Date: May 8, 2015

(87) PCT Pub. No.: WO2014/072089
PCT Pub. Date: May 15, 2014

(65) Prior Publication Data
US 2016/0242676 A1  Aug. 25, 2016

(30) Foreign Application Priority Data

Nov. 9, 2012  (DE) .................. 10 2012 220 468

(51) Int. Cl.
*A61B 5/107* (2006.01)
*G01B 17/00* (2006.01)
(Continued)

(52) U.S. Cl.
CPC .......... *A61B 5/1072* (2013.01); *A61B 5/7257* (2013.01); *G01B 5/061* (2013.01);
(Continued)

(58) Field of Classification Search
CPC ...... G01B 17/00; G01B 5/061; A61B 5/1072; A61B 5/7257; A61B 2560/0223; A61B 2562/0204
See application file for complete search history.

(56) References Cited

U.S. PATENT DOCUMENTS 4,913,157 A * 4/1990 Pratt, Jr. ............... A61B 8/0875
600/449
5,824,908 A * 10/1998 Schindel ................ G01N 29/11
73/598

(Continued)

FOREIGN PATENT DOCUMENTS

AT        397430 B     4/1994
AT        397439 B     4/1994
(Continued)

OTHER PUBLICATIONS

PCT International Search Report and Written Opinion from PCT Application No. PCT/EP2013/067022 entitled Length Measuring Device (dated May 21, 2015).

*Primary Examiner* — Isam A Alsomiri
*Assistant Examiner* — Amie M Ndure
(74) *Attorney, Agent, or Firm* — Hovey Williams LLP

(57) ABSTRACT

The invention relates to a length measuring device with a vernier caliper, a hollow profile, on which the vernier caliper is displaceably mounted externally so that it is capable of being brought into contact with an object to be measured in terms of its length, an inner slide, which is displaceably mounted inside the hollow profile, a magnet arrangement, which couples the vernier caliper and inner slide magnetically, so that the inner slide follows every movement of the vernier caliper along the hollow profile, a measuring means for measuring the position of the inner slide along the hollow profile, and a display, visible in the surrounding space of the hollow profile, of the length determined by the measuring means in accordance with the measured position of the inner slide.

20 Claims, 4 Drawing Sheets

Figure 3:
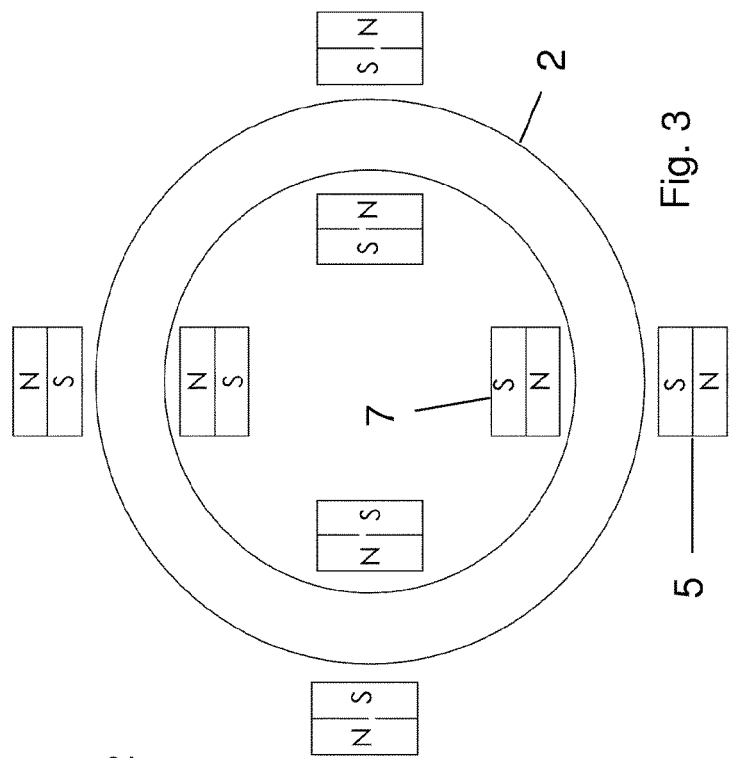

(51) Int. Cl.
*G01B 5/06* (2006.01)
*A61B 5/00* (2006.01)

(52) U.S. Cl.
CPC ...... *G01B 17/00* (2013.01); *A61B 2560/0223* (2013.01); *A61B 2562/0204* (2013.01)

(56) References Cited

U.S. PATENT DOCUMENTS

2005/0070801 A1* 3/2005 Yamashita ............ A61B 8/4281
600/459
2015/0174330 A1* 6/2015 Nagel ................... A61M 5/315
604/218

FOREIGN PATENT DOCUMENTS

| | | | | |
|---|---|---|---|---|
| AT | 401109 B | | 6/1996 | |
| DE | 3933116 A1 | | 4/1990 | |
| DE | 102010001886 | * | 2/2010 | ............ G01B 17/00 |
| DE | 102010001886 A1 | | 8/2011 | |
| EP | 0940658 A1 | | 9/1999 | |
| JP | S5972013 A | | 4/1984 | |
| JP | H02239843 | | 9/1990 | |
| JP | H05332757 A | | 12/1993 | |
| JP | 200461362 A | | 2/2004 | |
| JP | 200942142 A | | 2/2009 | |
| WO | 9817974 | | 4/1998 | |
| WO | WO-9817974 A1 | * | 4/1998 | ............... G01D 5/06 |

* cited by examiner

LENGTH MEASURING DEVICE

CROSS-REFERENCE TO RELATED APPLICATIONS

This is a National Phase Application pursuant to 37 C.F.R. § 371 of International Application No. PCT/EP2013/067022, filed Aug. 14, 2013, claiming priority from German Application No. DE 10 2012 220 468.7, filed Nov. 9, 2012, the entire disclosures of which are hereby incorporated by reference herein.

BACKGROUND OF THE INVENTION

1. Field of the Invention

The present invention relates to a length measuring device comprising a vernier caliper, a linear guide in the form of a hollow profile, on which the vernier caliper is displaceably mounted externally so that it is capable of being brought into contact with an object to be measured in terms of its length, an inner slide, which is displaceably mounted inside the hollow profile, a magnet arrangement which couples the vernier caliper and inner slide magnetically, so that the inner slide follows every movement of the vernier caliper along the hollow profile, a measuring means for measuring the position of the inner slide along the hollow profile, and a display, visible in the surrounding space of the hollow profile, of the length determined by the measuring means in accordance with the measured position of the inner slide.

2. Discussion of the Prior Art

The invention is directed in particular to length measuring devices for measuring the body height of individuals. Such length measuring devices are also designated stadiometers. A typical such length measuring device has a measuring rod, which is formed as a vertical linear guide for a vernier caliper (head slider). The measuring rod is aligned vertically and mounted on a wall or fixed to a platform. In order to measure the body height, the individual stands in front of the measuring rod, where after the head slider is pushed down on the measuring rod until it comes into contact with the head of the individual to be measured. A measuring scale having scale graduation marks is provided on the measuring rod. A reading unit is present in turn in the vernier caliper is, which registers the scale graduation marks as the vernier caliper is displaced on the measuring rod, and thus captures the incremental change in the position of the vernier caliper. The absolute height of a scale graduation mark can also be encoded in the scale graduation marks, so that the height of the head slider can be determined by using the reading unit, and is then displayed on a display on the vernier caliper.

Another type of length measuring device for the body height has an angled piece, which is held by an individual carrying out the measurement of the body length. One limb of the angled piece is held in contact on the head of the individual to be measured. From this limb in contact with the head, a second limb projects at a right angle, the angled piece being held in such a way that the second limb runs vertically, aimed at the floor. Provided in the second limb is a distance measuring means having an ultrasonic transducer which, from the propagation time of a transmitted ultrasound signal, which is reflected on the floor and runs back to the ultrasonic transducer, determines and displays the height above the floor of the first limb located in contact with the head of the individual to be measured, and therefore the body height. One disadvantage of this type of length measuring device consists in the fact that measurement inaccuracies can occur in that the individual carrying out the measurement does not keep the angled piece aligned exactly so that the second limb is aimed exactly vertically at the floor. Also disadvantageous is the fact that changing ambient conditions (e.g. dust or other contaminants in the air) or objects lying on the floor can falsify the measurement.

A further type of length measuring device has a platform, on which the individual to be measured stands, and a horizontal carrier fixedly suspended vertically above the individual to be measured. Fitted to the carrier is a distance measuring means based on ultrasonic wave propagation time, which is aimed at the head of the individual to be measured standing on the platform. The individual to be measured wears a cap, in order to ensure well-defined reflection of the ultrasound waves from the upper side of the head. From the distance of the upper side of the head of the individual to the distance measuring means fixedly installed vertically above the individual to be measured, the body length of the individual to be measured can be derived from the difference between the suspension height of the distance measuring means and the measured distance to the upper side of the head. Even this length measuring device is susceptible to faults, since the measurement can be falsified by changing ambient conditions and interfering influences in the open measuring distance between the ultrasonic transducer and the upper side of the head of the individual to be measured.

WO 98/17974 A1 discloses a length measuring device. This length measuring device is not configured as a length measuring device for individuals. Instead, the position of a vernier caliper is to be monitored. The length measuring device has a linear guide in the form of a hollow housing, on which the vernier caliper is displaceably mounted externally. In the interior of the housing, an inner slide is displaceably mounted therein. A magnet arrangement couples the vernier caliper and the inner slide magnetically, so that the inner slide follows every movement of the vernier caliper along the guide. The inner slide is in wiping contact with a linear potentiometer, in order to provide a voltage signal which is proportional to a position of the inner slide. From the potentiometer signal, the position of the inner slide along the linear guide, and therefore that of the vernier caliper coupled thereto, is derived. As a result of the measurement of the position of the inner slide in the interior of the housing, certain interfering factors such as smoke or dust which do not penetrate into the interior of the housing are certainly reduced in terms of their influence on the measurement accuracy. The potentiometer has wiping contacts, which produce abrasion and as a result wear over time. In order to counteract this, high-quality materials have to be used, which of course increases the production costs. However, even under these conditions, the wear can lead to impairment of the measurement accuracy.

SUMMARY

It is an object of the present invention to configure a length measuring device in such a way that it offers high measurement accuracy independent of changing ambient conditions and exhibits no wear-induced impairment of the measurement accuracy.

In order to achieve this object, use is made of a length measuring device comprising a vernier caliper, a linear guide, an inner slide, a magnet arrangement, a measuring means, and a display. The linear guide comprises a hollow profile, on which the vernier caliper is displaceably mounted externally so that the vernier caliper is capable of being brought into contact with an object to be measured in terms of an object length. The inner slide is displaceably mounted inside the hollow profile. The magnet arrangement couples the vernier caliper and inner slide magnetically, so that the inner slide follows every movement of the vernier caliper along the hollow profile. The measuring means is for measuring a position of the inner slide along the hollow profile. The display is visible a surrounding space of the hollow profile. The display is of a measured object length determined by the measuring means in accordance with the measured position of the inner slide. The hollow profile is provided with an end wall on at least one end. The inner slide substantially covers a cross section of the hollow profile in order to form an acoustic resonator in an interior of the hollow profile between the end wall and the inner slide. The measuring means includes a loudspeaker and a microphone in an interior of the acoustic resonator and a control and evaluation unit connected to the loudspeaker and the microphone. The control and evaluation unit is configured to cause the loudspeaker to issue an acoustic pulse, to record a pulse response of the acoustic resonator with the microphone, to determine from the pulse response of the acoustic resonator a basic frequency of the acoustic resonator, and to determine a length of the resonator and therefore the position of the inner slide along the hollow profile from the basic frequency of the acoustic resonator. Advantageous embodiments of the invention, including details of construction, are discussed herein.

According to the invention, provision is made for the hollow profile to be provided with an end wall on at least one end. Furthermore, the inner slide substantially covers the cross section of the hollow profile, so that a closed cavity, which can serve as an acoustic resonator, is formed in the interior of the hollow profile between the end wall and the inner slide. The measuring means has a loudspeaker and a microphone in the interior of the acoustic resonator between the end wall and the inner slide. A control and evaluation unit connected to the microphone and the loudspeaker is configured to cause the loudspeaker to issue an acoustic pulse and then to record the pulse response of the acoustic resonator with the microphone. The control and evaluation unit is further configured to determine the basic frequency from the pulse response of the acoustic resonator and to determine the length of the resonator and therefore the position of the inner slide along the hollow profile from the basic frequency. Here, basic frequency is understood to mean the lowest natural frequency, corresponding to a standing wave, the wavelength of which is twice as long as the acoustic resonator.

The inner slide substantially covers the cross section, in order to reflect incident sound waves effectively but can also have a small opening, e.g. to let air through during its movement.

In an advantageous embodiment, the control and evaluation unit is configured to transform the recorded pulse response of the acoustic resonator into a frequency spectrum by means of a Fourier transformation and to determine the basic frequency in the frequency spectrum. The Fourier transformation is preferably carried out in the form of a discrete Fourier transformation (DFT) or a fast Fourier transformation (FFT).

In a preferred embodiment, the control and evaluation unit is configured to determine the distance between two successive maxima for determining the basic frequency in the frequency spectrum. The distance can be used to establish the number of the harmonic involved at each maximum in the frequency spectrum. By using this information, a basic frequency can then be determined from each maximum, and this can then be averaged to form a basic frequency. It is also possible for a plurality of distances of successive maxima to be averaged in order to determine the basic frequency.

The control and evaluation unit is preferably configured to select the bandwidth of the acoustic pulse generated via the microphone such that the smallest wavelength contained is greater than twice the diameter of the hollow profile.

This ensures that the sound propagates in the hollow profile as a plane wave. In the case of shorter wavelengths, the sound could also be reflected between the walls of the hollow profile and therefore also excite further modes, of which the speed of sound in the longitudinal direction of the hollow profile is lower than the speed of sound of a plane wave; although these would not influence the measuring method so as to falsify the same, since they would certainly be separated during the Fourier transformation and then should merely not be used for the evaluation, the acoustic energy of such possible further modes would then not be useful for the measurement and would therefore be generated pointlessly, for which reason the excitation of a pure plane wave is preferred.

In a preferred embodiment, the hollow profile is also provided with a second end wall on the other end in order to form a second acoustic resonator in the interior of the hollow profile, between the second end wall and the inner slide. A second loudspeaker and a second microphone are arranged in this second acoustic resonator. The control and evaluation unit is further configured to cause the second loudspeaker to issue an acoustic pulse, to record the pulse response of the second acoustic resonator with the second microphone, from this to determine the basic frequency of the second acoustic resonator and, from the basic frequency, to determine the length of the second resonator and therefore the position of the inner slide along the hollow profile. In such a length measuring device, the control and evaluation unit can then advantageously also be configured to be able to carry out a calibration of the length determinations with the aid of the determined lengths of the acoustic resonator, the second acoustic resonator, the known length of the hollow profile between the end wall and the second end wall, and the known axial length of the inner slide.

In a preferred embodiment, the magnet arrangement has at least one permanent magnet on the vernier caliper and a permanent magnet on the inner slide, which are arranged in such a way that opposite poles of the two permanent magnets are aligned relative to each other so as to point toward each other. In each case four permanent magnets are preferably arranged on the inner slide and on the vernier caliper in such a way relative to one another that in each case a pair of permanent magnets on the vernier caliper and on the inner slide are aligned relative to each other with opposite poles pointing toward each other. Alternatively, the magnet arrangement has only one permanent magnet on one of the vernier caliper and inner slide, the other component of the vernier caliper and inner slide then containing ferromagnetic or paramagnetic material, so that the vernier caliper and inner slide are coupled magnetically.

The external dimensions of the inner slide are preferably matched to the internal dimensions of the hollow profile, so that the inner slide is seated in the hollow profile with the least possible play but such that it can slide. In a corresponding way, the internal dimensions of the vernier caliper are matched to the external dimensions of the hollow profile such that the vernier caliper is mounted on the hollow profile with the least possible play but such that it can slide.

BRIEF DESCRIPTION OF THE DRAWING FIGURES

Figure 2:
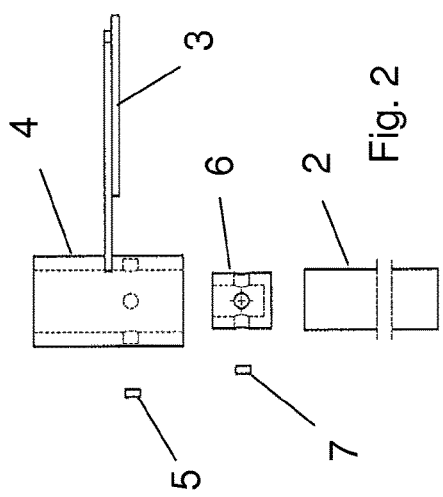
Figure 1:
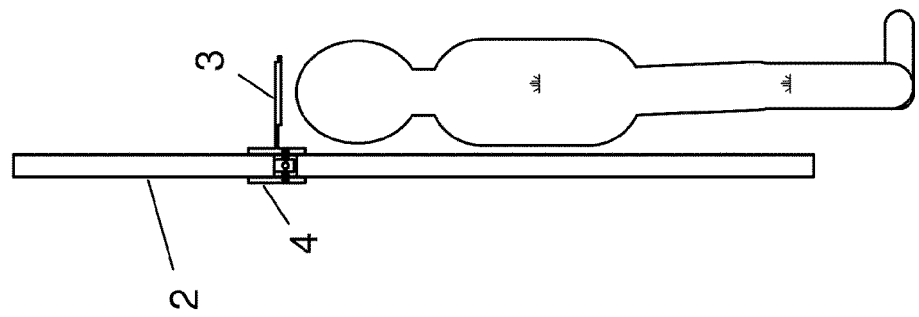
Figure 4:
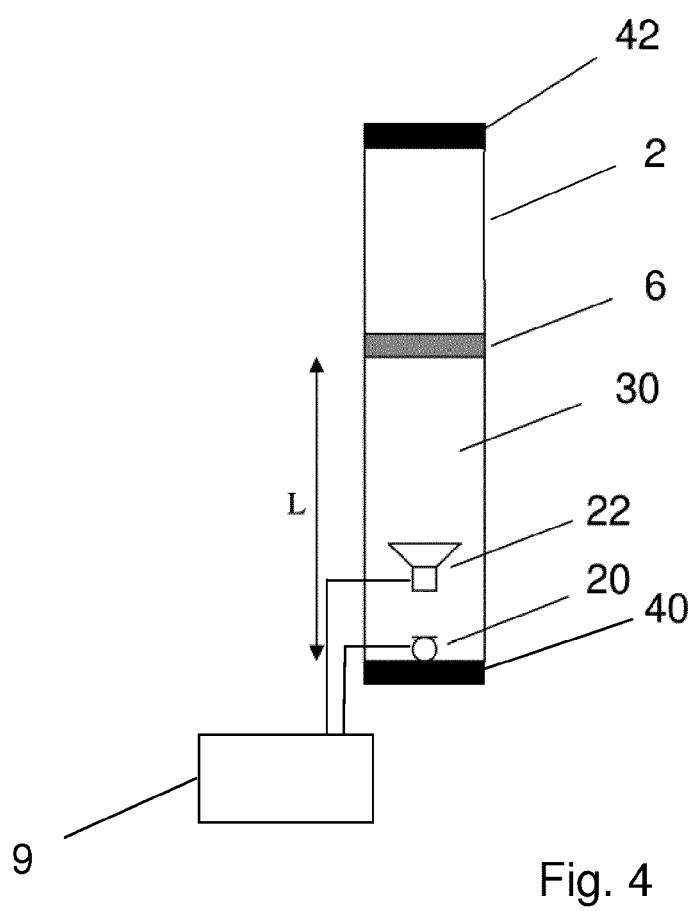
Figure 5:
Figure 6:
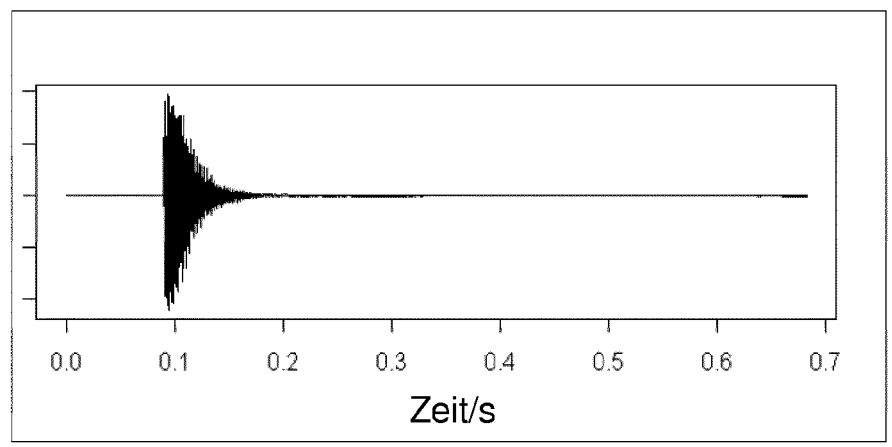
Figure 7:
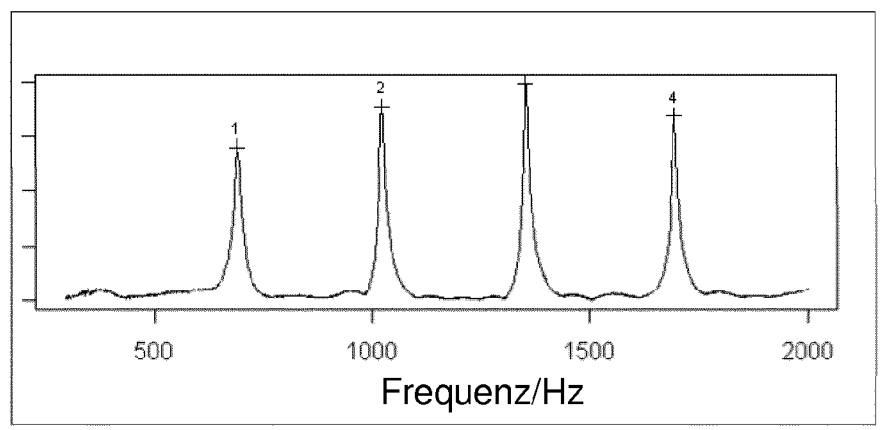
Figure 8:
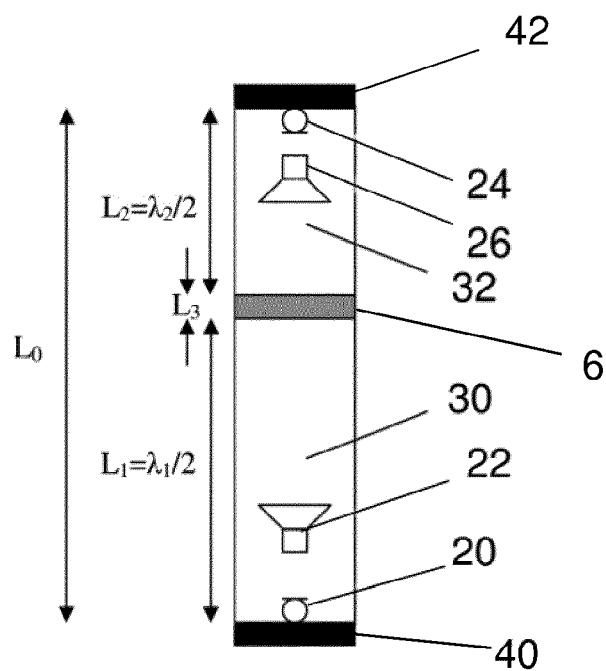

The invention will be described below by using an exemplary embodiment in conjunction with the drawings, in which:

FIG. 1 shows a schematic view of a length measuring device,

FIG. 2 shows an exploded illustration of parts of the length measuring device in the area of the vernier caliper in longitudinal section, FIG. 3 shows a cross-sectional view of the length measuring device in the area of the inner slide and vernier caliper, wherein the slide components themselves are not illustrated but only the permanent magnets arranged therein, FIG. 4 shows a schematic view of the hollow profile of a length measuring device in longitudinal section, FIG. 5 shows the amplitude variation over time of a signal exciting the loudspeaker to issue an acoustic pulse as a function of the time, FIG. 6 shows the recorded microphone signal of the pulse response of the acoustic resonator in the hollow profile, FIG. 7 shows the pulse response of the acoustic resonator from FIG. 6, transformed into a frequency spectrum, and FIG. 8 shows a schematic view of the hollow profile in longitudinal section of a further embodiment for a length measuring device.

DETAILED DESCRIPTION OF THE PREFERRED EMBODIMENTS

FIG. 1 shows a side view of a length measuring device which, for example, can be fixed to a wall. The length measuring device has a hollow profile 2 as a linear guide, on which a vernier caliper 4 which carries a head plate 3 is externally displaceably mounted. The vernier caliper 4 is lowered until the head plate 3 rests from above on the head of the individual to be measured.

In the hollow profile 2, which, in this exemplary embodiment, is in the shape of a circular ring in cross section, an inner slide 6 is displaceably mounted (see FIG. 2). The inner slide 6 is disk-like in cross section or, as illustrated here, is provided with a closed lower end wall, so that the inner slide covers the cross section of the hollow profile 2. The external dimensions of the inner slide 6 are matched to the internal dimensions of the hollow profile 2, so that the inner slide 6 is seated in the interior of the hollow profile 2 with the least possible play but such that it can slide. In a corresponding way, the internal dimensions of the vernier caliper 4 are matched to the external dimensions of the hollow profile 2, so that the vernier caliper 4 is mounted on the external circumference of the hollow profile 2 with the least possible play but such that it can slide.

FIG. 3 shows a cross section through the hollow profile 2 in the area of the vernier caliper and of the inner slide, wherein the vernier caliper components and the inner slide components themselves are not illustrated but only the magnet arrangement comprising a plurality of permanent magnets, which are introduced into the inner slide and the vernier caliper. In the inner slide 6, four permanent magnets 7 are inserted distributed around the circumference, being distributed at a spacing of ninety degrees (90°) relative to one another around the circumference. In a corresponding way, likewise four permanent magnets 5 are inserted into the vernier caliper 4, being arranged distributed around the external vernier caliper at corresponding spacings of ninety degrees (90°). Here, the arrangement of the permanent magnets is such that mutually opposite permanent magnets 5 and 7 of the vernier caliper 4 and of the inner slide 6 are aligned relative to one another with opposite poles. In the exemplary embodiment illustrated, this is achieved by the permanent magnets 7 of the inner slide being aligned with a magnetic pole, in this case with the North pole, toward the outside, while the permanent magnets 5 are likewise arranged to be aligned with this magnetic pole, here the North pole, toward the outside, so that in each case a pair of permanent magnets 5 and 7 are located opposite each other with opposite poles aimed toward each other. In this way, the vernier caliper 4 and the inner slide 6 are coupled magnetically to each other. As a result, the inner slide 6 follows every movement of the vernier caliper 4 along the hollow profile 2. In FIG. 2 only one of the permanent magnets 5 and 7 is respectively shown.

In principle, it is of course also possible for more or fewer than four permanent magnets per slide component to be provided, e.g. only respectively one permanent magnet in the vernier caliper 4 and the inner slide 6. It is even possible for only one magnet to be provided, either in the inner slide or in the vernier caliper 4, and for the other slide component without its own magnet to contain ferromagnetic or paramagnetic material, so that a magnetic attraction is effected between the inner slide 6 and the vernier caliper 4. The magnet or the magnets of the magnet arrangement is/are preferably permanent magnets, but in principle electromagnets can also be employed.

FIG. 4 shows a schematic longitudinal sectional view of a hollow profile 2 of a length measuring device. In this exemplary embodiment, the inner slide 6 is formed simply in the form of a disk and covers the cross section of the hollow profile 2. The hollow profile 2 is provided with a closed end wall 40 on the lower end, so that a closed chamber, which can be viewed as an acoustic resonator, is formed in the hollow profile, between the end wall 40 and the inner slide 6. The measuring means for determining the position of the inner slide 6 along the longitudinal direction of the hollow profile includes a loudspeaker 22 and a microphone 20, which are arranged in the interior of the acoustic resonator 30. The loudspeaker 22 and the microphone 20 are connected to a control and evaluation unit 9, which here is shown as arranged in the surrounding space of the hollow profile but can also be accommodated in the interior of the hollow profile. The control and evaluation unit 9 is a programmable data-processing means, which is configured to excite the loudspeaker 22 to issue an acoustic pulse and to record the resulting pulse response of the acoustic resonator 30 by recording the signal of the microphone 20. The control and evaluation unit 9 is further configured to determine the basic frequency $f_0$ of the resonator from the acoustic pulse response. This basic frequency $f_0$ has a wavelength $\lambda_0$ which corresponds to twice the length of the acoustic resonator (the simplest standing wave in the acoustic resonator 30 is a half-wave respectively having a velocity node at the end wall 40 and at the reflective wall of the inner slide 6). Given knowledge of the speed of sound c and of the basic frequency $f_0$, the length of the resonator can thus be determined:

$$L = \frac{c}{2 \cdot f_0}$$

Given broad-band excitation by means of an acoustic pulse, higher modes, the wavelengths of which are integer multiples of $\lambda_0/2$, are also excited in the acoustic resonator 30 in addition to the basic frequency. These modes can additionally be of benefit for the measuring method, as will be shown later.

FIG. 5 shows the time dependency of an excitation signal generated by the control and evaluation unit 9 for the loudspeaker 22 to issue an acoustic pulse. This signal preferably comprises a positive and negative half-wave with a substantially square form. The excitation signal does not have an ideal square form (which in principle would have a frequency spectrum with no upper limit), since the bandwidth of the pulse is limited. The bandwidth of the pulse should be selected such that the smallest wavelength contained is greater than twice the diameter of the hollow profile. Therefore, as already explained above, it is ensured that the sound propagates in the hollow profile as a plane wave. The length over time of a half-wave of the excitation signal should be greater than the period of the signal having the lowest frequency which is to be evaluated.

FIG. 6 shows the variation over time of the pulse response of the acoustic resonator, recorded by the microphone 20. In order to determine the basic frequency $f_0$ of the acoustic resonator therefrom, it is expedient to transform the acoustic pulse response from FIG. 6 into a frequency spectrum in order to determine the basic frequency $f_0$ in the frequency spectrum. The transformation into a frequency spectrum is carried out by means of a Fourier transformation. Possible digital signal processing methods relating to Fourier transformation are, for example, the discrete Fourier transformation (DFT) or the fast Fourier transformation (FFT), for the execution of which the control and evaluation unit 9 can be configured.

FIG. 7 now shows a portion of the frequency spectrum of the pulse response. Local maxima, which arise as a result of the excited eigenmodes, can be seen clearly therein. Said modes occur at integer multiples of the basic frequency $f_0$. The basic frequency can thus also be determined via the distances between adjacent modes in the frequency spectrum. This procedure has the advantage that the lower limiting frequency of the loudspeaker used can be selected to be greater than the actual basic frequency $f_0$ of the acoustic resonator that is to be determined. The lower limiting frequency of a loudspeaker is determined, amongst other things, by the size of its diaphragm. The larger said diaphragm is, the lower the limiting frequency can be. Since the loudspeaker is placed in the interior of the hollow profile, the smallest possible diaphragm diameter is intended. As a result, it is possible that the simplest standing wave in the acoustic resonator cannot be observed well with the present procedure, since the loudspeaker is not adequately able to generate the long wavelength required for this purpose. This effect can also be seen in FIG. 7, from which it emerges that the basic frequency is somewhat more than three hundred (300) Hz (distances between the successive maxima). At somewhat more than three hundred (300) Hz, however, in the frequency spectrum shown in FIG. 7 no usable maximum can be seen at the basic frequency of somewhat more than three hundred (300) Hz for the reason indicated.

Besides the exact determination of the basic frequency $f_0$, the speed of sound must be well known to the control and evaluation unit. Since the speed of sound has a temperature dependence, it is recommended to measure the temperature $\vartheta$ inside the resonator and to calculate the current speed of sound based thereon. This can be done, for example, by using the equation $$c = 331.5 \frac{m}{s} \cdot \sqrt{1 + \frac{\vartheta}{273.15° \text{ C.}}}$$

A further embodiment, with which the accuracy of the measurement of the measuring means can be improved, is illustrated in FIG. 8. In FIG. 8, as in FIG. 4, a schematic view of the hollow profile in the longitudinal section of the length measuring device is shown. As in the embodiment according to FIG. 6, an acoustic resonator 30, in which there are a loudspeaker 22 and a microphone 20 (the control and evaluation unit connected to the latter has been left out in order to simplify the illustration) is formed in the hollow profile 2. Furthermore, a second acoustic resonator 32 is formed in the hollow profile, between the opposite second end wall 42 of the hollow profile and the inner slide 6. Located therein are a second loudspeaker 26 and a second microphone 24, which are likewise connected to the control and evaluation unit. By means of this arrangement, the length measurement can be calibrated, since the length of the hollow profile between the end walls 40 and 42 and the axial length of the inner slide 6 are known. Under the assumption that the speed of sound in the first acoustic resonator 30 and in the second acoustic resonator 32 is the same (which assumes that the temperature in the two acoustic resonators is the same), the speed of sound can be determined by means of the following equations:

$$L_0 = L_1 + L_2 + L_3$$

$$L_0 - L_3 = L_1 + L_2 = \frac{c}{2 \cdot f_{01}} + \frac{c}{2 \cdot f_{02}} = \frac{c}{2}\left(\frac{1}{f_{01}} + \frac{1}{f_{02}}\right)$$

$$c = \frac{2 \cdot (L_0 - L_3)}{\left(\frac{1}{f_{01}} + \frac{1}{f_{02}}\right)} = 2 \cdot (L_0 - L_3) \cdot \frac{(f_{01} \cdot f_{02})}{f_{01} + f_{02}}$$

with
$L_0$ length of the hollow profile between the end walls 40, 42
$L_1$ length of the acoustic resonator 30
$L_2$ length of the upper, second resonator 32
$L_3$ axial length of the inner slide 6 in the longitudinal direction of the hollow profile
$f_{01}$ basic frequency of the resonator 30
$f_{02}$ basic frequency of the second resonator 32.

The speed of sound determined in this way can then be used, for example, to determine the length of the one acoustic resonator 30:

$$L_1 = \frac{c}{2 \cdot f_{01}}$$

LIST OF REFERENCE NUMERALS

2 Hollow profile
3 Head plate
4 Vernier caliper
5 Permanent magnets of the vernier caliper
6 Inner slide
7 Permanent magnets of the inner slide
9 Control and evaluation unit
20 Microphone
22 Loudspeaker 24 Second microphone
26 Second loudspeaker
30 Acoustic resonator
32 Second acoustic resonator
40 End wall
42 Second end wall

The invention claimed is:

1. A length measuring device for measuring the physical height of a person, said length measuring device comprising:
   a vernier caliper,
   a linear guide comprising a hollow profile, on which the vernier caliper is displaceably mounted externally so that the vernier caliper is capable of being brought into contact on the head of the person to be measured in terms of physical height,
   an inner slide, which is displaceably mounted inside the hollow profile,
   a magnet arrangement which couples the vernier caliper and inner slide magnetically, so that the inner slide follows every movement of the vernier caliper along the hollow profile,
   a measuring means for measuring a position of the inner slide along the hollow profile, and
   a display, visible in a surrounding space of the hollow profile, of a person's measured physical height determined by the measuring means in accordance with the measured position of the inner slide,
   wherein the hollow profile is provided with an end wall on at least one end,
   wherein the inner slide substantially covers a cross section of the hollow profile in order to form an acoustic resonator in an interior of the hollow profile between the end wall and the inner slide, and
   wherein the measuring means includes a loudspeaker and a microphone in an interior of the acoustic resonator and a control and evaluation unit connected to the loudspeaker and the microphone,
   said control and evaluation unit configured to cause the loudspeaker to issue an acoustic pulse, to record a pulse response of the acoustic resonator with the microphone, to determine from the pulse response of the acoustic resonator a basic frequency of the acoustic resonator, and to determine a length of the resonator and therefore the position of the inner slide along the hollow profile from the basic frequency of the acoustic resonator.

2. The length measuring device as claimed in claim 1, wherein the control and evaluation unit is configured to transform the measured pulse response of the acoustic resonator into a frequency spectrum by means of a Fourier transformation and to determine the basic frequency of the acoustic resonator in the frequency spectrum.

3. The length measuring device as claimed in claim 2, wherein the control and evaluation unit is configured to carry out a discrete Fourier transformation or a fast Fourier transformation for the Fourier transformation.

4. The length measuring device as claimed in claim 3, said frequency spectrum of the acoustic resonator presenting a plurality of maxima,
   wherein the control and evaluation unit is configured to determine a distance between two successive ones of said maxima as an estimated value for the basic frequency of the acoustic resonator, in relation to said plurality of maxima; to use the estimated value to establish a number of a harmonic involved at each of said maxima; from the number of the harmonic involved at each of said maxima to determine a basic frequency of the acoustic resonator in relation to each of the maxima examined; and to combine the basic frequencies of the acoustic resonator to form an average basic frequency of the acoustic resonator.

5. The length measuring device as claimed in claim 2, said frequency spectrum of the acoustic resonator presenting a plurality of maxima,
   wherein the control and evaluation unit is configured to determine a distance between two successive ones of said maxima as an estimated value for the basic frequency of the acoustic resonator, in relation to said plurality of maxima; to use the estimated value to establish a number of a harmonic involved at each of said maxima; from the number of the harmonic involved at each of said maxima to determine a basic frequency of the acoustic resonator in relation to each of the maxima examined; and to combine the basic frequencies of the acoustic resonator to form an average basic frequency of the acoustic resonator.

6. The length measuring device as claimed in claim 1,
   wherein the control and evaluation unit is configured to select a bandwidth of the acoustic pulse such that a smallest wavelength contained is greater than twice a diameter of the hollow profile.

7. The length measuring device as claimed in claim 1,
   wherein the hollow profile is also provided with a second end wall on an other end in order to form a second acoustic resonator in the interior of the hollow profile, between the second end wall and the inner slide, and
   wherein the measuring means includes a second loudspeaker and a second microphone in an interior of the second acoustic resonator, and
   wherein the control and evaluation unit is configured to cause the second loudspeaker to issue a second acoustic pulse, to record a pulse response of the second acoustic resonator with the second microphone, to determine a basic frequency of the second acoustic resonator based on the pulse response of the second acoustic resonator, and to determine a length of the second acoustic resonator from the basic frequency of the second acoustic resonator.

8. The length measuring device as claimed in claim 7,
   wherein the control and evaluation unit is configured to carry out a calibration of the length determinations with the aid of the determined lengths of the acoustic resonator and the second acoustic resonator, a known length of the hollow profile between the end wall and the second end wall, and a known axial length of the inner slide.

9. The length measuring device as claimed in claim 7,
   wherein the control and evaluation unit is configured to transform the measured pulse response of the acoustic resonator into a frequency spectrum by means of a Fourier transformation and to determine the basic frequency of the acoustic resonator in the frequency spectrum,
   wherein the control and evaluation unit is configured to transform the measured pulse response of the second acoustic resonator into a second frequency spectrum by means of a second Fourier transformation and to determine the basic frequency of the second acoustic resonator in the second frequency spectrum.

10. The length measuring device as claimed in claim 9,
    wherein the control and evaluation unit is configured to carry out a discrete Fourier transformation or a fast Fourier transformation for the Fourier transformation, wherein the control and evaluation unit is configured to carry out a discrete Fourier transformation or a fast Fourier transformation for the second Fourier transformation.

11. The length measuring device as claimed in claim 10, said frequency spectrum of the acoustic resonator presenting a plurality of first maxima,
wherein the control and evaluation unit is configured to determine a distance between two successive ones of said first maxima as an estimated value for the basic frequency of the acoustic resonator, in relation to said plurality of first maxima; to use the estimated value for the basic frequency of the acoustic resonator to establish a number of a harmonic involved at each of said first maxima; from the number of the harmonic involved at each of said first maxima to determine a basic frequency of the acoustic resonator in relation to each of the first maxima examined; and to combine the basic frequencies of the acoustic resonator to form an average basic frequency of the acoustic resonator,
said second frequency spectrum of the second acoustic resonator presenting a plurality of second maxima,
wherein the control and evaluation unit is configured to determine a distance between two successive ones of said second maxima as an estimated value for the basic frequency of the second acoustic resonator, in relation to said plurality of second maxima; to use the estimated value for the basic frequency of the second acoustic resonator to establish a number of a harmonic involved at each of said second maxima; from the number of the harmonic involved at each of said second maxima to determine a basic frequency of the second acoustic resonator in relation to each of the second maxima examined; and to combine the basic frequencies of the second acoustic resonator to form an average basic frequency of the second acoustic resonator.

12. The length measuring device as claimed in claim 9, said frequency spectrum of the acoustic resonator presenting a plurality of first maxima,
wherein the control and evaluation unit is configured to determine a distance between two successive ones of said first maxima as an estimated value for the basic frequency of the acoustic resonator, in relation to said plurality of first maxima; to use the estimated value for the basic frequency of the acoustic resonator to establish a number of a harmonic involved at each of said first maxima; from the number of the harmonic involved at each of said first maxima to determine a basic frequency of the acoustic resonator in relation to each of the first maxima examined; and to combine the basic frequencies of the acoustic resonator to form an average basic frequency of the acoustic resonator,
said second frequency spectrum of the second acoustic resonator presenting a plurality of second maxima,
wherein the control and evaluation unit is configured to determine a distance between two successive ones of said second maxima as an estimated value for the basic frequency of the second acoustic resonator, in relation to said plurality of second maxima; to use the estimated value for the basic frequency of the second acoustic resonator to establish a number of a harmonic involved at each of said second maxima; from the number of the harmonic involved at each of said second maxima to determine a basic frequency of the second acoustic resonator in relation to each of the second maxima examined; and to combine the basic frequencies of the second acoustic resonator to form an average basic frequency of the second acoustic resonator.

13. The length measuring device as claimed in claim 7, wherein the control and evaluation unit is configured to select a bandwidth of the acoustic pulse and a bandwidth of the second acoustic pulse such that, for each, a smallest wavelength contained is greater than twice a diameter of the hollow profile.

14. The length measuring device as claimed in claim 7, wherein the magnet arrangement includes at least one permanent magnet on the vernier caliper and a permanent magnet on the inner slide, which are arranged in such a way that opposite poles of the two permanent magnets are aligned relative to each other so as to point toward each other.

15. The length measuring device as claimed in claim 14, wherein four of said permanent magnets are arranged on the inner slide and four of said permanent magnets are arranged on the vernier caliper in such a way relative to one another that a plurality of pairs of permanent magnets are formed on the vernier caliper and on the inner slide,
said pairs of permanent magnets being aligned relative to each other with opposite poles pointing toward each other.

16. The length measuring device as claimed in claim 7, wherein the magnet arrangement includes a permanent magnet on one of the vernier caliper and inner slide, and
wherein the other of the vernier caliper and inner slide contains ferromagnetic or paramagnetic material.

17. The length measuring device as claimed in claim 1, wherein the magnet arrangement includes at least one permanent magnet on the vernier caliper and a permanent magnet on the inner slide, which are arranged in such a way that opposite poles of the two permanent magnets are aligned relative to each other so as to point toward each other.

18. The length measuring device as claimed in claim 17, wherein four of said permanent magnets are arranged on the inner slide and four of said permanent magnets are arranged on the vernier caliper in such a way relative to one another that a plurality of pairs of permanent magnets are formed on the vernier caliper and on the inner slide,
said pairs of permanent magnets being aligned relative to each other with opposite poles pointing toward each other.

19. The length measuring device as claimed in claim 1, wherein the magnet arrangement includes a permanent magnet on one of the vernier caliper and inner slide, and
wherein the other of the vernier caliper and inner slide contains ferromagnetic or paramagnetic material.

20. The length measuring device as claimed in claim 1, wherein the measuring means is further connected to a temperature sensor in the interior of the hollow profile, and
wherein the control and evaluation unit is configured to arrange for a temperature-corrected speed of sound to be incorporated into the determination of the length of the acoustic resonator from the basic frequency of the acoustic resonator.

* * * * *